US00PP20395P2

(12) United States Plant Patent

Pieters

(10) Patent No.: US PP20,395 P2

(45) Date of Patent: Oct. 6, 2009

(54) *CHRYSANTHEMUM* PLANT NAMED 'PPP RHN 07'

(50) Latin Name: *Chrysanthemum morifolium*
Varietal Denomination: PPP RHN 07

(75) Inventor: Dirk Pieters, Oostnieuwkerke (BE)

(73) Assignee: Paraty BVBA, Oostnieuwkerke (BE)

( * ) Notice: Subject to any disclaimer, the term of this patent is extended or adjusted under 35 U.S.C. 154(b) by 0 days.

(21) Appl. No.: 12/218,785

(22) Filed: Jul. 18, 2008

(51) Int. Cl.
*A01H 5/00* (2006.01)

(52) U.S. Cl. ..... Plt./290

(58) Field of Classification Search ..... Plt./290, Plt./287

See application file for complete search history.

*Primary Examiner*—June Hwu
(74) *Attorney, Agent, or Firm*—Mark P. Bourgeois

(57) ABSTRACT

A new and distinct *Chrysanthemum* plant cultivar is disclosed, characterized by large decorative type inflorescences, consistent flowering response to short days, blooming consistently after 49 days of short day length, orange inflorescences with an orange-red center, free branching habit, and a consistent natural season flowering habit during the first week of September.

1 Drawing Sheet

Latin name of the genus and species: *Chrysanthemum morifolium.*

Variety denomination: 'PPP RHN 07'.

BACKGROUND OF THE INVENTION

The new cultivar 'PPP RHN 07' is a product of a cross between the male parent 'Yutaka' and the female parent 'Simone' (neither are patented in the United States.) The new cultivar was discovered and selected by Dirk Pieters in September of 2004 in Oostnieuwkerke, Belgium.

Asexual reproduction of the new cultivar 'PPP RHN 07' by terminal cuttings was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP RHN 07' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP RHN 07.' These characteristics in combination distinguish 'PPP RHN 07' as a new and distinct *Chrysanthemum* cultivar:

1. Large, orange decorative-type inflorescences with a orange-red center;
2. Consistent flowering response to short days, blooming consistently after 49 days of short day length;
3. Free branching habit; and
4. Consistent natural season flowering habit during the first week of September.

Plants of the new cultivar 'PPP RHN 07' are similar to plants of the male parent variety 'Yutaka' in most horticultural characteristics, however plants of the new cultivar 'PPP RHN 07' has a wider plant spread. Also, the new cultivar 'PPP RHN 07' has orange ray florets compared to the red ray florets of the male parent. Finally, 'PPP RHN 07' naturally blooms one month earlier than 'Yutaka.'

Plants of the new cultivar 'PPP RHN 07' are similar to plants of the female parent variety, 'Simone' in most horticultural characteristics, however plants of the new cultivar 'PPP RHN 07' have a wider plant spread. Also, the new cultivar 'PPP RHN 07' has orange ray florets compared to the yellow ray florets of the female parent. Additionally, 'PPP RHN 07' has a decorative-type inflorescence compared to the daisy-type inflorescence of 'Simone.' Finally, 'PPP RHN 07' naturally blooms two weeks earlier than the female parent.

In comparison to the commercially available variety 'GEDI THREE PORA' (U.S. Plant Pat. No. 17,067), 'PPP RHN 07' is smaller in height and has a wider plant spread. Additionally, the new variety 'PPP RHN 07' has spoon ray florets and more ray florets per inflorescence. Further, the inflorescences of the new variety 'PPP RHN 07' are a lighter orange with a dark red center compared to the pure dark orange inflorescences of 'GEDI THREE PORA.' Finally, the new variety 'PPP RHN 07' has longer inflorescence longevity.

BRIEF DESCRIPTION OF THE PHOTOGRAPH

The accompanying photograph illustrates in full color a typical plant of 'PPP RHN 07' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP RHN 07' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium* 'PPP RHN 07.'
Commercial classification: Garden-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 22 cm.
Plant spread: Approximately 39 cm.
Growth rate: Moderate.
Branching characteristics: Free Branching.
Length of lateral branches: Approximately 16 cm.
Number of Leaves per Lateral branch: Approximately 26.
Age of plant described: Approximately 140 days.

FOLIAGE

Leaf:
*Arrangement.*—Alternate single.
*Average Length.*—Approximately 3.5 cm.
*Average width.*—Approximately 2.7 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 1 cm.
*Color.*—Young foliage upper side: Near Green 137A. Young foliage under side: Near Green 137C. Mature foliage upper side: Near Green 137A. Mature foliage under side: Near Green 137C.
*Venation.*—Type: Palmately net. Venation color upper side: Near Green 138C. Venation color under side: Near Green 138C.
Petiole:
*Average length.*—Approximately 1.8 cm.
*Color.*—Near Green 138B.
*Diameter.*—Approximately 0.3 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately first week in September.
*Number of inflorescences per lateral branch.*—Approximately 24.
*Inflorescence diameter.*—Approximately 4.5 cm.
*Inflorescence depth.*—Approximately 1.5 cm.
*Inflorescence longevity on plant.*—Approximately 28 to 34 days.
*Persistence.*—Persistent.
Ray Florets:
*Appearance.*—Matte.
*Texture.*—Smooth.
*Average number of ray florets per inflorescence.*—182.
*Shape.*—Spoon.
*Aspect.*—Flat.
*Margin.*—Entire.
*Apex.*—Obtuse.
*Base.*—Fused along 50% of its length.
*Length.*—Approximately 1.9 cm.
*Width.*—Approximately 0.4 cm.
*Color.*—Upper surface at first opening: Near Greyed-Red 178A. Upper surface at maturity: Near Greyed-Orange 167A. Upper surface at fading: Near Greyed-Orange 168D. Under surface at first opening: Near Greyed-Red 178A. Under surface at maturity: Near Greyed-Orange 173C. Under surface at fading: Near Greyed-Orange 168D. Center ray florets: Near Greyed-Red 179A throughout maturity and fading.
Disc florets:
*Appearance.*—Shiny.
*Texture.*—Smooth.
*Average number of florets per disc.*—Approximately 18.
*Shape.*—Cylindric.
*Apex.*—Obtuse.
*Average length.*—Approximately 0.5 cm.
*Average width.*—Approximately 0.1 cm.
*Color.*—At first opening: Near Green-Yellow 1A. At maturity: Near Yellow-Orange 13A. At fading: Near Yellow-Orange 13A.
Peduncle:
*Length.*—At terminal end (shortest): Approximately 4.6 cm. At lateral end (longest): Approximately 8.5 cm.
*Angle to stem.*—Acute.
*Strength.*—Moderate.
*Color.*—Near Green 138A.
*Habit.*—Upright.
*Diameter.*—Approximately 0.2 cm.
*Surface texture.*—Lightly pubescent.
Inflorescence bud:
*Length.*—Approximately 1 cm.
*Diameter.*—Approximately 0.7 cm.
*Form.*—Globular.
*Color.*—Near Greyed-Red 181A.
Involucral bracts (phyllaries):
*Appearance.*—Matte.
*Texture.*—Lightly pubescent.
*Number.*—Approximately 25.
*Shape.*—Oblanceolate.
*Margin.*—Entire.
*Apex.*—Acute.
*Length.*—Approximately 0.5 cm.
*Width.*—Approximately 0.3 cm.
*Color.*—Upper side: Near Green 137A. Under side: Near Green 137B.

REPRODUCTIVE ORGANS

Ray florets:
*Number of pistils per floret.*—1.
*Stigma shape.*—2 branched.
*Stigma color.*—Near Yellow 12A.
*Style color.*—Near Yellow-Green 154C.
*Style length.*—Approximately 0.3 cm.
*Stamens.*—Absent.
Disc florets:
*Number of pistils per floret.*—1.
*Stigma shape.*—Cylindric.
*Stigma color.*—Near Yellow 12A.

*Style length.*—Approximately 0.2 cm.
*Style color.*—Near Yellow-Green 154D.
*Number of stamens per floret.*—Approximately 5.
*Anther shape.*—Tubular.
*Anther color.*—Near Yellow 12A.
*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP RHN 07' as herein illustrated and described.

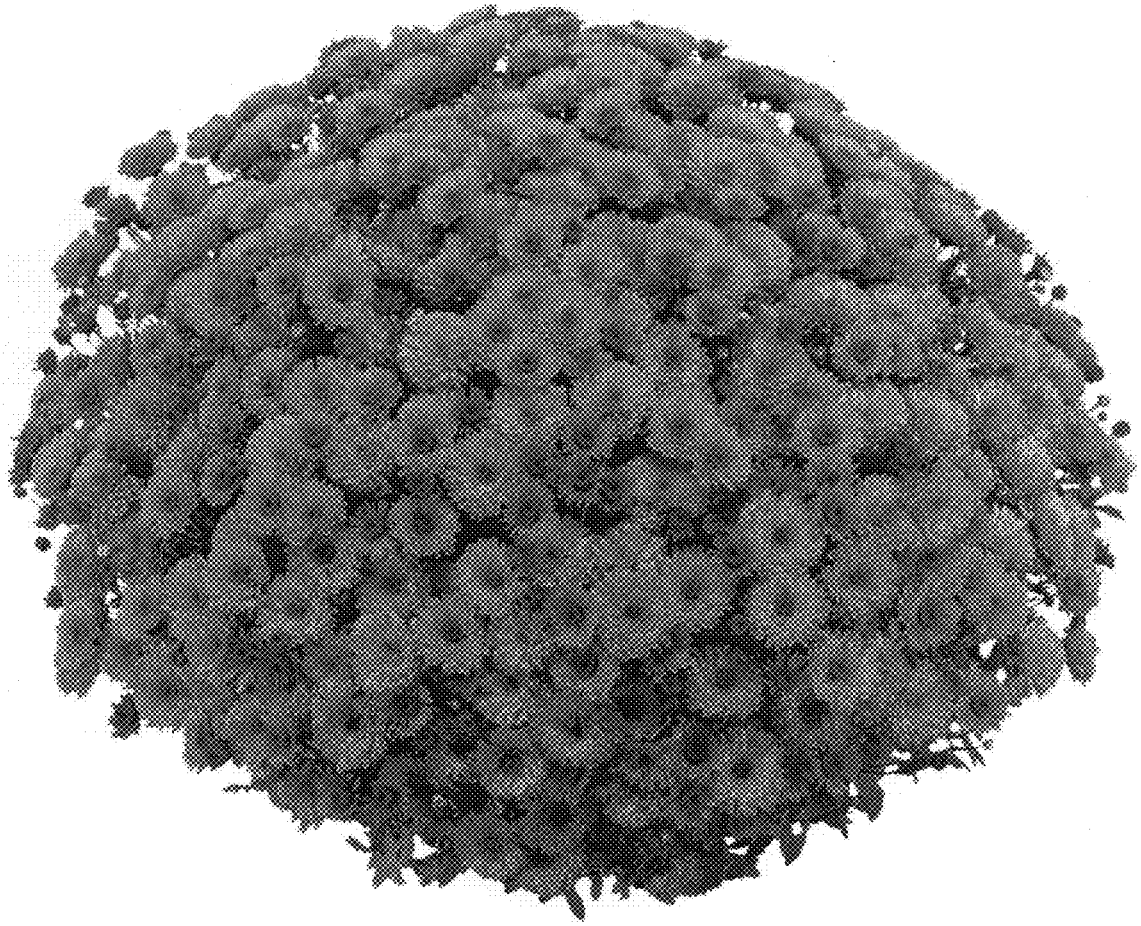

* * * * *